United States Patent
Hahne et al.

(10) Patent No.: US 10,183,152 B2
(45) Date of Patent: Jan. 22, 2019

(54) CINCHING PERITONEAL DIALYSIS CATHETER

(71) Applicant: Cook Medical Technologies LLC, Bloomington, IN (US)

(72) Inventors: Kalub Hahne, West Lafayette, IN (US); Adam Shields, Lafayette, IN (US); Keith Milner, West Lafayette, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 423 days.

(21) Appl. No.: 14/938,159

(22) Filed: Nov. 11, 2015

(65) Prior Publication Data
US 2016/0166805 A1 Jun. 16, 2016

Related U.S. Application Data

(60) Provisional application No. 62/091,202, filed on Dec. 12, 2014.

(51) Int. Cl.
A61M 25/02 (2006.01)
A61M 1/12 (2006.01)
A61M 25/00 (2006.01)

(52) U.S. Cl.
CPC ............ A61M 25/02 (2013.01); A61M 1/125 (2014.02); A61M 25/0017 (2013.01);
(Continued)

(58) Field of Classification Search
CPC .. A61M 25/02; A61M 1/285; A61M 25/0017; A61M 25/0043; A61M 2025/0213; A61M 2205/32
(Continued)

(56) References Cited

U.S. PATENT DOCUMENTS 4,368,737 A    1/1983  Ash
4,391,276 A *  7/1983  Lazarus ............. A61M 25/007
                                                      604/266
(Continued)

FOREIGN PATENT DOCUMENTS

EP    0 134 340 A1    3/1985
GB    2 245 496 A     1/1992

OTHER PUBLICATIONS

European Patent Application 15198116.0 Extended Search Report dated May, 2, 2016, 5 pages.

Primary Examiner — Manuel Mendez
(74) Attorney, Agent, or Firm — Woodard, Emhardt, Moriarty, McNett & Henry, LLP

(57) ABSTRACT

Described are peritoneal catheter devices and methods for positioning these devices in a medical patient. The peritoneal catheter includes a catheter tube having a proximal end portion opposite a distal end portion, a stationary flange attached to the catheter tube near the distal end portion, and a mobile flange positioned on the catheter tube between the stationary flange and the proximal end portion. In use, the stationary flange is positioned to cover a hole in the rectus muscle and the mobile flange is selectively moved along the catheter tube to sandwich the rectus muscle of the patient between the stationary flange and the mobile flange. Optionally an interior cuff is mounted on the catheter tube adjacent to the stationary flange but between the stationary flange and the mobile flange and wherein the selectively positioning the mobile flange includes sandwiching the interior cuff between the stationary flange and the mobile flange.

25 Claims, 4 Drawing Sheets

(52) U.S. Cl.
CPC . *A61M 25/0043* (2013.01); *A61M 2025/0213* (2013.01); *A61M 2205/32* (2013.01)

(58) Field of Classification Search
USPC .......................... 604/175, 174, 265, 266, 28
See application file for complete search history.

(56) References Cited

U.S. PATENT DOCUMENTS

| | | | |
|---|---|---|---|
| 4,687,471 A | | 8/1987 | Twardowski et al. |
| 4,886,502 A | | 12/1989 | Poirier et al. |
| 4,950,259 A | * | 8/1990 | Geary ................... A61M 1/285 |
| | | | 604/175 |
| 5,171,227 A | | 12/1992 | Twardowski et al. |
| 5,484,420 A | * | 1/1996 | Russo ................... A61M 25/02 |
| | | | 604/174 |
| 5,984,896 A | | 11/1999 | Boyd |
| 9,107,810 B2 | * | 8/2015 | Bailey ............... A61M 39/0247 |
| 2006/0155250 A1 | | 7/2006 | Endo et al. |
| 2016/0038650 A1 | * | 2/2016 | Griffith ................... A61L 29/16 |
| | | | 604/265 |
| 2016/0302999 A1 | * | 10/2016 | El-Haddad .......... A61J 15/0015 |

* cited by examiner

CINCHING PERITONEAL DIALYSIS CATHETER

CROSS REFERENCE TO PREVIOUS APPLICATION

This application claims the benefit of U.S. Provisional Patent Application No. 62/091,202 filed Dec. 12, 2014, which is hereby incorporated by reference.

BACKGROUND

The present disclosure relates generally to medical technology and in particular aspects to devices and methods for positioning a peritoneal catheter in a body of a patient to begin a medical treatment immediately after placement of the peritoneal catheter.

One use of a peritoneal catheter is during end-stage renal disease (ESRD) to instill dialysis fluid into the peritoneum into the peritoneal cavity. The peritoneal catheter must be inserted through the skin, subcutaneous fat, rectus muscle and parietal peritoneum into the peritoneal cavity. Most peritoneal catheters are equipped with a polyester synthetic cuff that is placed within the rectus muscle which encourages incorporation of the cuff into the surrounding tissue. This ingrowth requires 2 to 3 weeks to heal completely. If the site does not heal properly or heal completely, the dialysis fluid is able to leak out of the peritoneal cavity, through the rectus muscle and along the length of the peritoneal catheter. This leakage causes a variety of problems including inflammation of the tunneled area and infection by providing a means of bacterial colonization into the tunnel tract.

Another cause of improper healing is movement of the peritoneal catheter. If the polyester synthetic cuff does not properly affix the peritoneal catheter by tissue ingrowth, the cuff may slide into the cavity. Under these conditions the peritoneal catheter will be able to move, the peritoneal catheter tunnel site will be open to the dialysate solution and the cuff and catheter tunnel can become a site of bacterial colonization.

One type of catheter is available which does not require the 2 to 3 weeks of healing before the initiation of peritoneal dialysis; however this catheter has shortcomings also. This catheter has a silicone ball and flange at the site of a cuff. The ball and flange are pushed into the rectus muscle and the flange is sutured to the muscle. This effectively closes the peritoneal cavity from the tunneled catheter site. This type of catheter requires dilation of the insertion site to create adequate space for the ball and flange which creates a larger hole. In addition, suturing the flange to the muscle increases catheter placement time. This method requires additional time-consuming measures and increases the size of the hole in the muscle.

There remain needs for improved and/or alternative systems and methods for positioning a peritoneal catheter in a body of a patient to begin a medical treatment immediately after placement of the peritoneal catheter by closing the peritoneal cavity off from the tunneled catheter thus decreasing the risk of leakage and tunneling infections. The present disclosure is addressed to those needs.

SUMMARY

The present disclosure provides, in certain aspects, unique methods and devices for positioning a peritoneal catheter in a body of a patient.

In one embodiment, a distal tip of a catheter tube of the peritoneal catheter is advanced through the body of a patient to a target site in a peritoneal cavity of the patient and then a stationary flange circumferentially surrounding and mounted on the catheter tube is advanced through a hole in the rectus muscle of the patient. Next, the hole in the rectus muscle of the patient is covered with the stationary flange and a mobile flange circumferentially surrounding and positioned on the catheter tube is advanced into the body of the patient. The mobile flange can be selectively positioned on the catheter tube to sandwich the rectus muscle between the stationary flange and the mobile flange.

In another embodiment, a peritoneal catheter includes a catheter tube having a proximal end portion opposite a distal end portion. This embodiment includes a stationary flange attached to the catheter tube near the distal end portion wherein the stationary flange circumferentially surrounds the catheter tube and a mobile flange is positioned on the catheter tube between the stationary flange and the proximal end portion wherein the mobile flange circumferentially surrounds the catheter tube. The mobile flange is configured for selective placement along the catheter tube. In one form, the mobile flange is configured to slide along or cinch down the catheter tube.

In an alternative embodiment, a peritoneal catheter includes a catheter tube having a proximal end portion opposite a distal end portion. This embodiment includes a stationary flange attached to the catheter tube near the distal end portion wherein the stationary flange circumferentially surrounds the catheter tube and a mobile flange is positioned on the catheter tube between the stationary flange and the proximal end portion wherein the mobile flange circumferentially surrounds the catheter tube. The mobile flange is configured for selective placement along the catheter tube. The peritoneal catheter also includes an interior cuff mounted on the catheter tube between the stationary flange and the mobile flange wherein the interior cuff is positioned adjacent the stationary flange. Additionally in some forms this alternative embodiment includes an outer cuff mounted on the catheter tube and positioned between the mobile flange and the proximal end portion of the catheter tube.

In yet another embodiment, the peritoneal catheter includes a catheter tube, a stationary flange, a mobile flange, and an interior cuff as described above, and additionally at least one bead positioned on the catheter tube between the interior cuff and the mobile flange wherein the bead is configured to retain the mobile flange adjacent to and/or pressed against the interior cuff. Optionally, the peritoneal catheter includes two beads positioned in a lineal or a substantial perpendicular orientation along a longitudinal axis of the catheter tube. The bead is configured to retain the mobile flange against the interior cuff.

In any embodiment, the interior cuff can be made of a biomaterial to accommodate tissue ingrowth or alternatively a sheet of biomaterial can be wrapped around the interior cuff to accommodate tissue ingrowth.

Further forms, objects, features, aspects, benefits, advantages, and embodiments of the present disclosure will become apparent from a detailed description and drawings provided herewith.

DESCRIPTION OF THE SELECTED EMBODIMENTS

Figure 1:
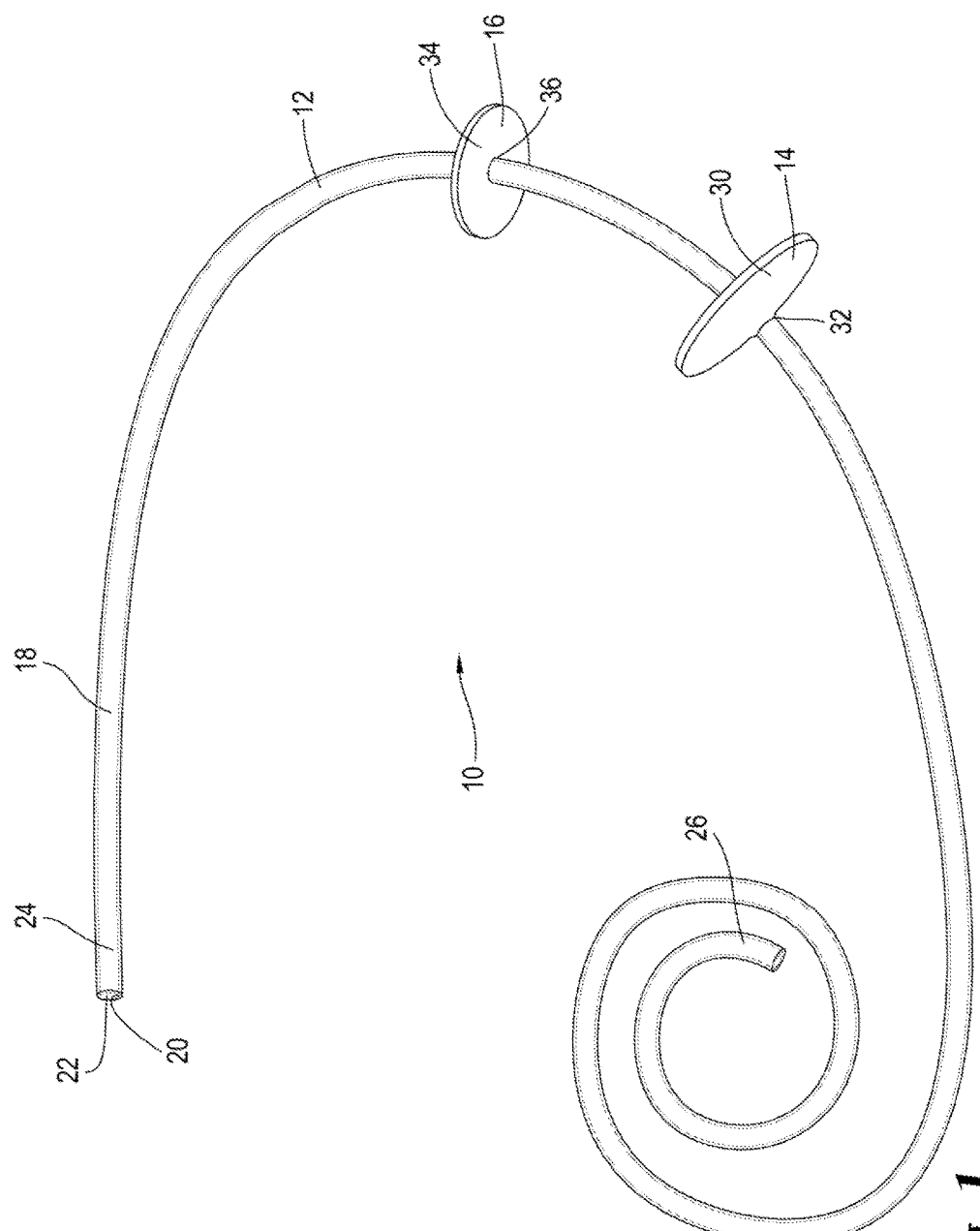
FIG. 1 is a top perspective view of an inventive peritoneal catheter according to a first embodiment of the present disclosure.

While the present disclosure may be embodied in many different forms, for the purpose of promoting an understanding of the principles of the present disclosure, reference will now be made to the embodiments illustrated in the drawings, and specific language will be used to describe the same. It will nevertheless be understood that no limitation of the scope of the disclosure is thereby intended. Any alterations and further modifications in the described embodiments and any further applications of the principles of the present disclosure as described herein are contemplated as would normally occur to one skilled in the art to which the disclosure relates.

In certain aspects, the present disclosure provides unique devices and methods for positioning a peritoneal catheter in a body of a patient to begin a medical treatment. The present disclosure provides for a peritoneal catheter including a catheter tube having a proximal end portion opposite a distal end portion, a stationary flange attached to the catheter tube near the distal end portion wherein the stationary flange circumferentially surrounds the catheter tube, and a mobile flange positioned on the catheter tube between the stationary flange and the proximal end portion wherein the mobile flange circumferentially surrounds the catheter tube. Alternative embodiments include one or more of an interior cuff, an outer cuff, and one or more beads positioned on the catheter tube. In any embodiment, the mobile flange is configured for selective placement along the catheter tube. Briefly describing the method of positioning the peritoneal catheter in a body of a patient to begin a medical treatment includes advancing the distal end portion of the catheter tube of the peritoneal catheter through the body of the patient to a target site in a peritoneal cavity of the patient, and then advancing the stationary flange circumferentially surrounding and mounted on the catheter tube through a hole in the rectus muscle of the patient. Next, a medical practitioner covers the hole in the rectus muscle of the patient with the stationary flange and thereafter the practitioner advances the mobile flange circumferentially surrounding and positioned on the catheter tube into the body of the patient. Finally, the medical practitioner selectively positions the mobile flange along the length of the catheter tube to a position on the catheter tube to thereby sandwich the rectus muscle between the stationary flange and the mobile flange.

Relative movement of the mobile flange along the length of the catheter tube enables proper positioning of the catheter tube in the rectus muscle sheath to substantially prevent movement of the peritoneal catheter in the body of a patient. The seal provided by the stationary flange over the hole in the rectus muscle sheath also allows immediate initiation of peritoneal dialysis. The seal provided by the stationary flange prevents dialysate leakage before healing of the hole in the rectus muscle and incorporation of the stationary flange is completed. Moreover, the mobile flange also provides a seal and a physical barrier that occludes the peritoneal cavity from the tunnel site from the skin surface. Simultaneously, the mobile flange allows for proper healing of the rectus muscle and tissue ingrowth around the catheter tube. These benefits are highly advantageous during ESRD to instill dialysis fluid immediately into the peritoneal cavity without additional waiting time.

Figure 2:
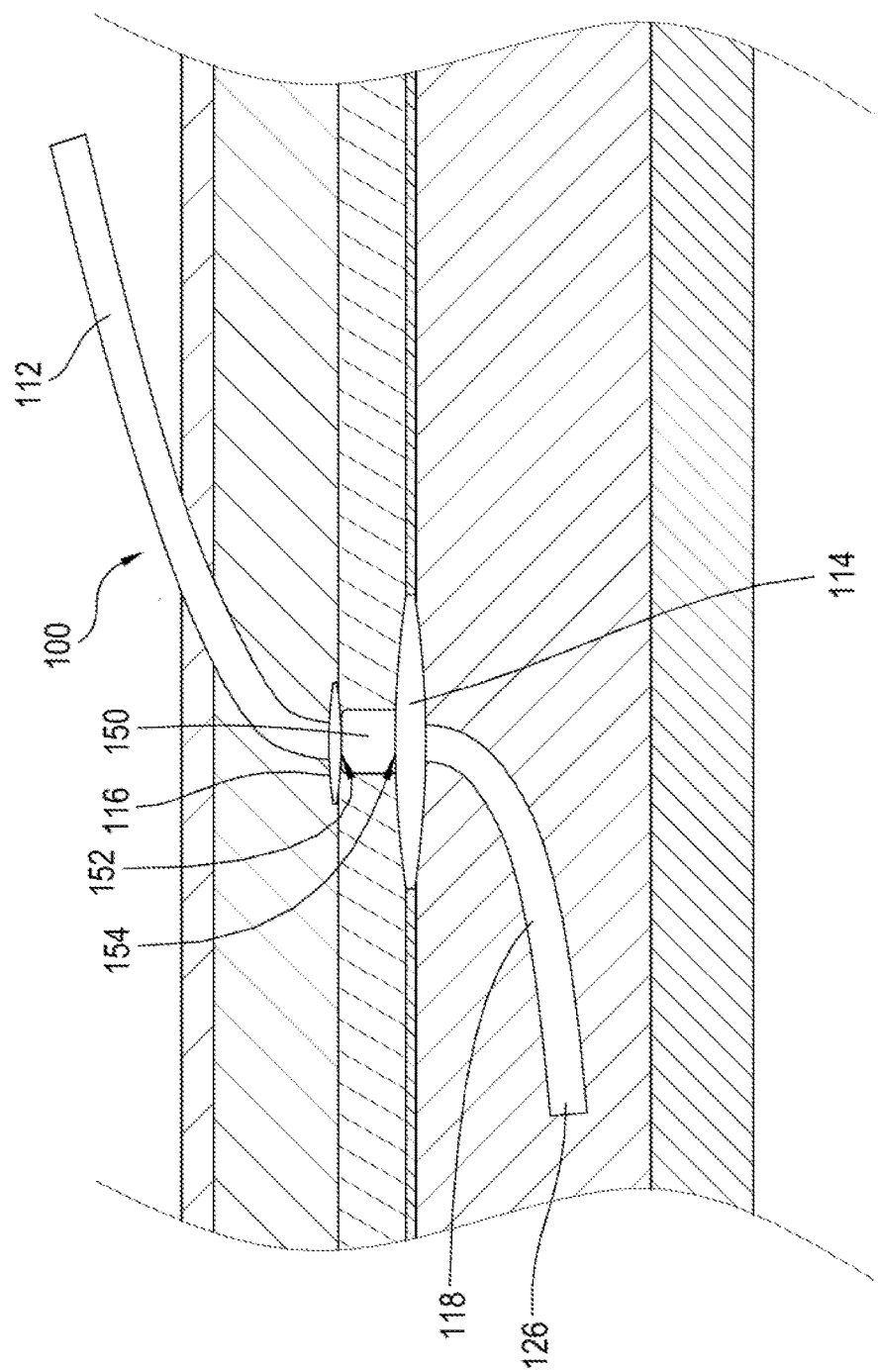
FIG. 2 is a side view of an inventive peritoneal catheter according to a second embodiment of the present disclosure implanted in a medical patient.
Figure 3:
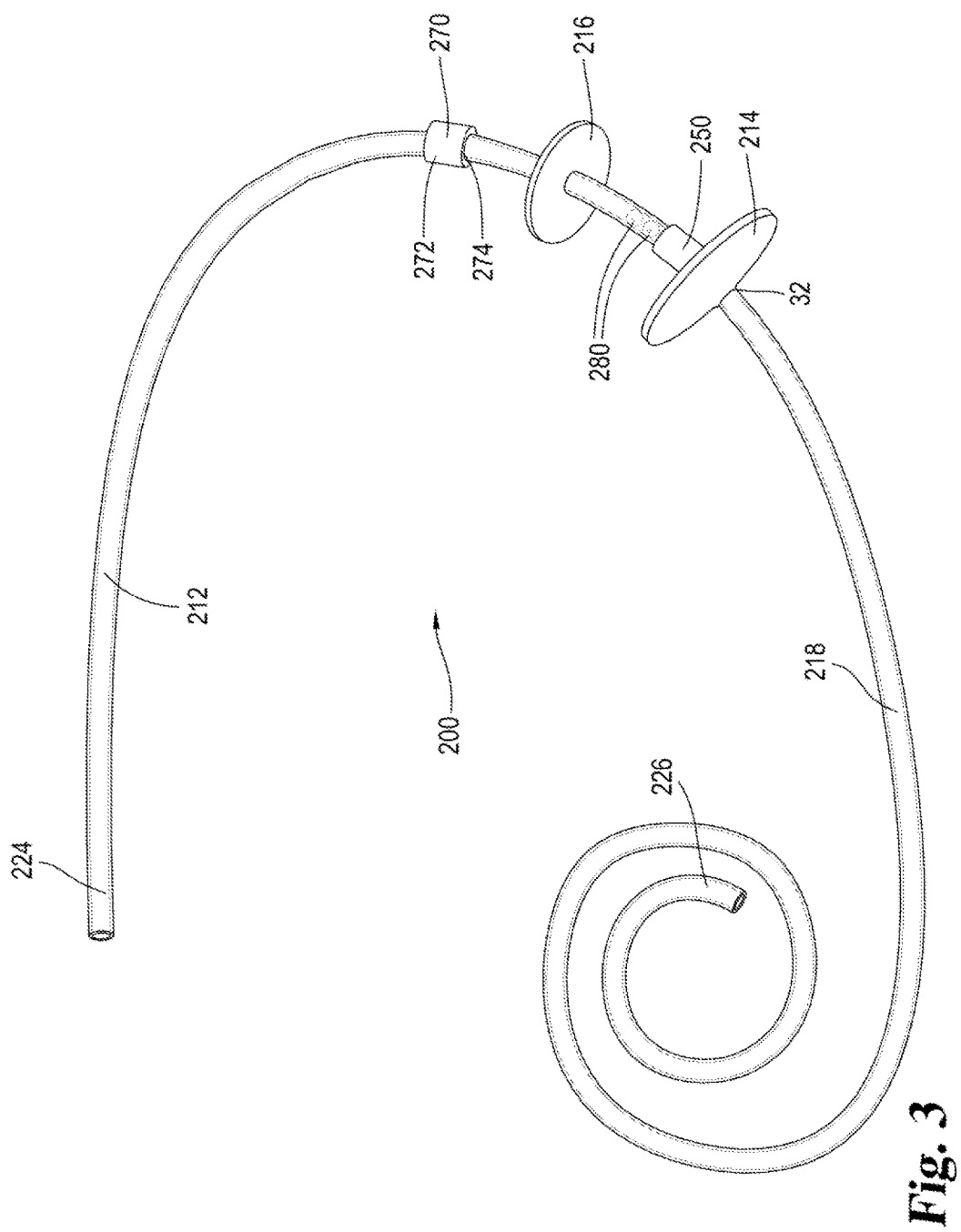
FIG. 3 is a top perspective view of an inventive peritoneal catheter according to a third embodiment of the present disclosure.

FIG. 1 illustrates one non-limiting example of a peritoneal catheter according to one embodiment of the present disclosure. FIG. 2 illustrates a second non-limiting example of a peritoneal catheter according to another embodiment of the present disclosure that includes at least an interior cuff. Additionally in those embodiments that utilize an interior cuff on the catheter tube, the relative movement of the mobile flange along the length of the catheter tube to engage and press against the interior cuff ensures the interior cuff is properly positioned within the rectus muscle sheath. This proper positioning of the interior cuff allows for proper tissue ingrowth and healing of the sheath muscle. FIG. 3 illustrates another non-limiting example of a peritoneal catheter according to another embodiment of the present disclosure that also includes at least an interior cuff, an outer cuff, and one or more beads on a catheter tube.

With reference now to FIG. 1, there is shown a peritoneal catheter 10 according to one embodiment of the present disclosure. In this illustrative arrangement, the peritoneal catheter 10 includes a catheter tube 12, a stationary flange 14 attached to the catheter tube 12, and a mobile flange 16 positioned on the catheter tube 12 and configured for movement along the catheter tube 12.

In this illustrative embodiment as seen in FIG. 1, the hollow catheter tube 12 defines an outer surface 18 and an inner surface 20 surrounding a lumen 22 that extends axially between proximal and distal ends 24 and 26, respectively. The lumen 22 is sized to permit delivery of medication, dialysate solution, or other solutions as directed by a physician therethrough directly into the patient's peritoneal cavity. In one form, the thickness of the catheter tube 12 from the inner surface 20 to the outer surface 18 is about 0.010 inch. The diameter of lumen 22 is substantially uniform through most of catheter tube 12 in the illustrated embodiment. It is estimated that particularly useful diameters of lumen 22 range from about 0.05 inch to about 0.2 inch. Of course, there may be applications that require larger or smaller dimensions for catheter tube 12. The catheter tube 12 can be curved or straight as may be desired or necessary for a particular medical procedure.

In some embodiments, the catheter tube 12 is made of or includes a biocompatible radiopaque material, so as to give the physician the option to visualize catheter tube 12 by fluoroscopy or X-rays. For example, catheter tube 12 can be made of silicone, polyurethane, or any other biocompatible material in which barium sulfate or another radiopaque material is mixed or suspended. As another example, distal end 26 of catheter tube 12 may be configured to include a guidance element for visualizing, guiding and/or positioning the rotational orientation of catheter tube 12 within the patient. Such guidance elements include one or more markers, sensors, and/or emitters. For instance, the distal end 26 and/or other part(s) of catheter tube 12 may include a radiopaque marker (e.g. a bead of biocompatible metal) to permit visualization or other location of such part(s), in particular their position and/or orientation within a patient's body.

Figure 4:
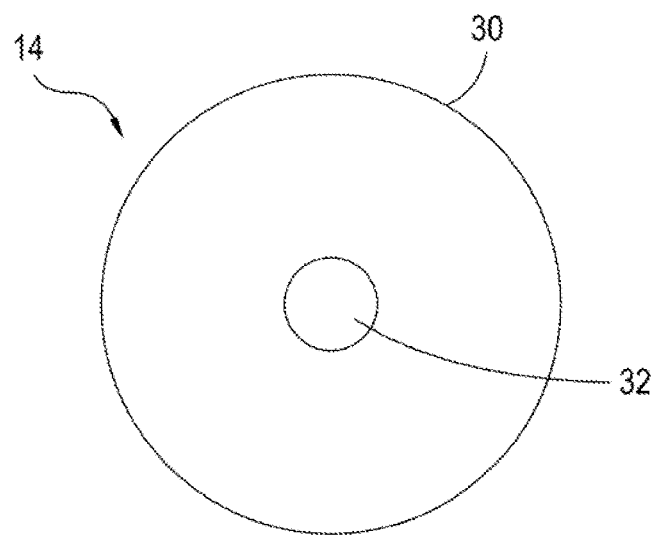
FIG. 4 is a front view of the inventive stationary flange as illustrated in FIG. 1.

Turning now to the stationary flange 14 (illustrated in FIG. 4) that is attached to the catheter tube 12 (illustrated in FIG. 1), the stationary flange 14 circumferentially surrounds the catheter tube 12 wherein the stationary flange 14 has a wall 30 that defines an opening 32 sized to snugly receive outer surface 18 of the catheter tube 12. The stationary flange 14 is positioned near or close to the distal end 26 of the catheter tube 12. In the illustrated embodiment, the stationary flange 14 is attached to the catheter tube 12 in a perpendicular orientation relative to a longitudinal axis of the catheter tube 12. In another embodiment, the stationary flange 14 is attached to the catheter tube 12 in a non-perpendicular orientation relative to a longitudinal axis of the catheter tube 12. The wall 30 is substantially flat; however in other embodiments the wall 30 is concave or convex relative to the longitudinal axis of the catheter tube 12.

As illustrated, the opening 32 has a corresponding diameter and shape to receive the outer surface 18 of catheter tube 12. The opening 32 is sized to snugly receive the outer surface 18 of the catheter tube 12 such that there are no gaps or space between the opening 32 and the outer surface 18 of the catheter tube 12. The illustrated embodiment of the stationary flange 14 has a diameter between the range of about 1 centimeter to about 8 centimeters and a thickness of between about 0.5 millimeters to about 3 millimeters. In one embodiment, the stationary flange 14 has a diameter of about 27 millimeters. The stationary flange 14 has a circular or disc shape; however in other embodiments the stationary flange 14 can be shaped differently such as oval, polygonal, or other curved shape. Moreover in other embodiments, the stationary flange 14 has a fluted disk shape wherein the stationary flange 14 is deployed into the patient in a folded configuration and then expands to a substantially flat circular disc once it is inside the patient's body. In any embodiment, the stationary flange 14 is sized to cover a hole in a rectus muscle of a patient. The stationary flange 14 can be the same size as the mobile flange 16 or the stationary flange 14 can be larger than the mobile flange 16.

The stationary flange 14 is attached to the catheter tube 12 with any of adhesive, glue, silicone, or any other means that ensures the stationary flange 14 does not move relative to the catheter tube 12. The stationary flange 14 is made of silicone, plastic, polyethylene, polyurethane, polytetrafluoroethylene, polyvinylidene fluoride, polyvinylidene difluoride, polypropylene, other biocompatible materials, or any combination of these materials.

Figure 5:
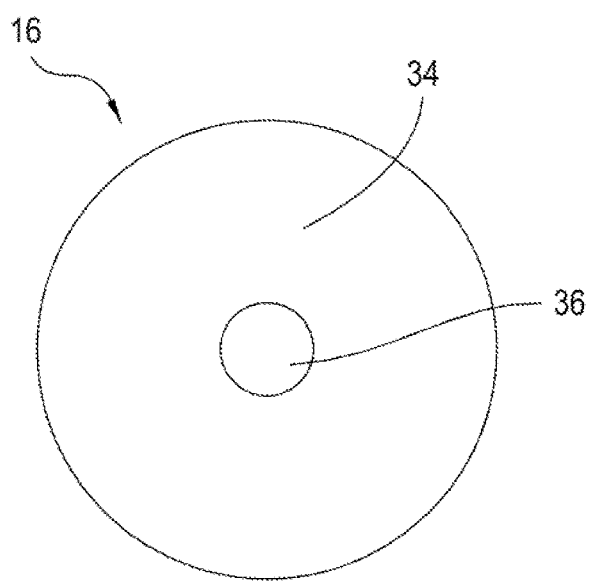
FIG. 5 is a front view of the inventive mobile flange as illustrated in FIG. 1.

The mobile flange 16 as illustrated in FIG. 5 is also positioned on the catheter tube 12 but unlike the stationary flange 14, the mobile flange 16 is configured for movement along the length of the catheter tube 12. The mobile flange 16 circumferentially surrounds the catheter tube 12 wherein the mobile flange 16 has a wall 34 that defines an opening 36 sized to snugly receive outer surface 18 of the catheter tube 12. The mobile flange 16 is positioned on the catheter tube 12 at a location between the stationary flange 14 and the proximal end 24 of the catheter tube 12. In the illustrated embodiment, the mobile flange 16 is positioned on the catheter tube 12 wherein the mobile flange 16 is configured to slide or cinch over the outer surface 18 of catheter tube 12 to move along the length of the catheter tube 12. In one embodiment, the force required to push the mobile flange 16 along the length of and over the outer surface 18 of the catheter tube 12 is about 4 Newtons or 0.9 pounds. When the peritoneal catheter 10 is positioned in a medical patient, the mobile flange 16 is selectively positioned on the catheter tube 12 to a location on the catheter tube 12 that sandwiches the rectus muscle between the stationary flange 14 and the mobile flange 16. In one embodiment, the mobile flange 16 is in a non-perpendicular orientation relative to the longitudinal axis of the catheter tube 12. In another embodiment, the mobile flange 16 is positioned on the catheter tube 12 in a perpendicular orientation relative to the longitudinal axis of the catheter tube 12. In another embodiment, when the peritoneal catheter 10 is positioned in a medical patient, the mobile flange 16 is moved along the length of the catheter tube 12 to contact the rectus muscle such that the mobile flange 16 is substantially parallel to the stationary flange 14.

The wall 34 is substantially flat; however in other embodiments the wall 34 is concave or convex relative to the longitudinal axis of the catheter tube 12. As illustrated, the opening 36 has a corresponding diameter and shape to snugly receive the outer surface 18 of catheter tube 12. As such, the opening 36 corresponds to the shape and size of a portion of the catheter tube 12 over which the mobile flange 16 slides. There are no openings or gaps between the opening 36 and the outer surface 18 of the catheter tube 12. The illustrated embodiment of the mobile flange 16 has a diameter between the range of about 1 centimeter to about 8 centimeters and a thickness of between about 0.5 millimeters to about 3 millimeters. In one embodiment, the mobile flange 16 has a diameter of about 22 millimeters. The mobile flange 16 has a circular or disc shape; however in other embodiments the mobile flange 16 can be shaped differently such as oval, polygonal, or other curved shape. In any embodiment, the mobile flange 16 is sized to cover a hole in a rectus muscle of a patient. The mobile flange 16 can be the same size as the stationary flange 14 or the mobile flange 16 can be smaller than the stationary flange 14. The mobile flange 16 is made of silicone, plastic, polyethylene, polyurethane, polytetrafluoroethylene, polyvinylidene fluoride, polyvinylidene difluoride, polypropylene, or any biocompatible material, or any combination of these materials.

Turning now to positioning the peritoneal catheter 10 in a body of a patient to begin a medical treatment includes making a small incision in the skin of a medial patient and forming a micropuncture through the rectus muscle and parietal peritoneum of the patient to create a tunnel or opening into the peritoneal cavity. Next an over the wire catheter tube is advanced through the tunnel and a dilator is passed through the tunnel to increase the diameter of the tunnel or dilate out the tunnel. The dilator is removed from the tunnel. Other techniques can be used as are known in the medical field for insertion of a catheter tube into the body of the patient. Next, the distal end 26 of the catheter tube 12 is advanced through the tunnel of the body of the patient to a target site in a peritoneal cavity of the patient. Next, the stationary flange 14 circumferentially surrounding and mounted on the catheter tube 12 is advanced through the tunnel to a hole in the rectus muscle of the patient. Next, a medical practitioner covers the hole in the rectus muscle of the patient with the stationary flange 14. In one embodiment, the medical practitioner pushes the stationary flange 14 through the hole in the rectus muscle and then pulls the stationary flange 14 back or away from the body of the medical patient to create a seal over the hole. Thereafter the practitioner advances or pushes the mobile flange 16 circumferentially surrounding and positioned on the catheter tube 12 into the body of the patient. Finally, the medical practitioner selectively positions or cinches the mobile flange 16 along the length of the catheter tube 12 to a position or location on the catheter tube 12 to thereby sandwich the rectus muscle between the stationary flange 14 and the mobile flange 16. The mobile flange 16 also covers the hole in the rectus muscle to create a seal over the hole to begin a medical treatment or peritoneal dialysis immediately. The peritoneal catheter 10 is immobilized so that the medical treatment can begin immediately by preventing dialysate leakage before the healing and incorporation is completed. No sutures are needed to secure the peritoneal catheter 10 in the medical patient with the use of the stationary flange 14 and the mobile flange 16.

Turning now to a second embodiment of a peritoneal catheter 100 illustrated in FIG. 2, the peritoneal catheter 100 is similar in all aspects to the peritoneal catheter 10 described above except for the addition of an interior cuff 150 mounted on a catheter tube 112. As such, the peritoneal catheter 100 includes a catheter tube 112, a stationary flange 114, a mobile flange 116, and an interior cuff 150. The catheter tube 112, stationary flange 114, and the mobile flange 116 are similar in all aspects to the catheter tube 12, stationary flange 14, and mobile flange 16, respectively, therefore for the sake of brevity these elements will not be described again.

The interior cuff 150 is mounted on the catheter tube 112 between the stationary flange 114 and the mobile flange 116 wherein the interior cuff 150 is positioned adjacent to and in contact with the stationary flange 114. In one form, the interior cuff 150 is wrapped around an outer surface 118 of the catheter tube 112 to form a tube-like shape that spans between a distal end 152 to a proximal end 154. Alternatively, the interior cuff 150 is formed in a tube shape with an inner diameter that corresponds to the diameter and outer surface 118 of the catheter tube 112. In this alternative embodiment, there is no space or gaps between the inner diameter of the interior cuff 150 and the outer surface 118 of the catheter tube 112. The length of the interior cuff 150 corresponds to about the thickness of a rectus muscle of a medical patient. The length of the interior cuff 150 ranges from about 5 millimeters to about 50 millimeters; however other lengths can be used as desired by a medical practitioner. The interior cuff 150 has a wall thickness that spans between the proximal and distal ends 152 and 154, respectively.

Turning now to a discussion of materials that can be used in interior cuff 150, such materials can include any suitable biocompatible material. Generally, the material may include synthetic materials, such as a polyester felt, polyethylene terephthalate, polyester, or reconstituted or naturally-derived collagenous materials, or a combination of materials. Such biocompatible materials that are at least bioresorbable will provide advantages in embodiments of the invention, with materials that are bioremodelable and promote cellular invasion and ingrowth providing particular advantage. Illustratively, remodelable materials may be used in this context to promote cellular growth.

Bioremodelable materials of the invention can be provided by collagenous extracellular matrix (ECM) materials possessing biotropic properties, including in certain forms angiogenic collagenous ECM materials. For example, suitable collagenous materials include ECM materials, such as submucosa, renal capsule membrane, dermal collagen, dura mater, pericardium, serosa, facia lata, peritoneum, or basement membrane layers including liver basement membrane. The preferred medical graft products of the invention will include submucosa, such as submucosa derived from a warm-blooded vertebrate. Suitable submucosa materials for these purposes include, for instance, intestinal submucosa, including small intestinal submucosa, stomach submucosa, urinary bladder submucosa, and uterine submucosa. Mammalian submucosa materials are preferred. In particular, submucosa materials derived from animals raised for meat or other product production, e.g. pigs, cattle or sheep, will be advantageous. Porcine submucosa provides a particularly preferred material for use in the present invention, especially porcine small intestine submucosa (SIS), more especially porcine small intestine submucosa retaining substantially its native cross-linking.

The submucosa or other ECM material used in the interior cuff embodiments described herein, such as interior cuff 150, can be derived from any suitable organ or other biological structure, including for example submucosa derived from the alimentary, respiratory, intestinal, urinary or genital tracts of warm-blooded vertebrates. Submucosa useful in the present invention can be obtained by harvesting such tissue sources and delaminating the submucosa from smooth muscle layers, mucosal layers, and/or other layers occurring in the tissue source. For additional information concerning submucosa useful in certain embodiments of the present invention, and its isolation and treatment, reference can be made, for example, to U.S. Pat. Nos. 4,902,508, 5,554,389, 5,993,844, 6,206,931, and 6,099,567.

Submucosa or other ECM materials can be derived from any suitable organ or other tissue source, usually sources containing connective tissues. The ECM materials processed for use in certain embodiments will typically include abundant collagen, most commonly being constituted of at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in embodiments of the invention will include significant amounts of such interspersed, non-collagenous solids that are readily ascertainable under light microscopic examination. Such non-collagenous solids can constitute a significant percentage of the dry weight of the ECM material in certain embodiments, for example at least about 1%, at least about 3%, and at least about 5% by weight in various embodiments of the invention.

The submucosa or other ECM material used in illustrative embodiments may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels. In some instances, it is preferable for a portion of an interior cuff, such as the outer portion, to have an angiogenic character so as to further secure the cuff within the body of the patient and/or resist infection. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

As prepared and used, the submucosa material or any other ECM material may optionally retain and/or include growth factors or other bioactive components native to the source tissue. For example, the submucosa or other ECM material may include one or more growth factors such as basic fibroblast growth factor (FGF-2), transforming growth factor beta (TGF-beta), epidermal growth factor (EGF), and/or platelet derived growth factor (PDGF). As well, submucosa or other ECM material used in embodiments of the invention may include other biological materials such as heparin, heparin sulfate, hyaluronic acid, fibronectin and the like. Thus, generally speaking, the submucosa or other ECM material may include a bioactive component that induces, directly or indirectly, a cellular response such as a change in cell morphology, proliferation, growth, protein or gene expression. In certain preferred embodiments of the invention, the ECM material will exhibit the capacity to promote angiogenesis.

Further, in addition or as an alternative to the inclusion of native bioactive components, non-native bioactive components, such as those synthetically produced by recombinant technology or other methods, may be incorporated into the submucosa or other ECM material. These non-native bioactive components may be naturally-derived or recombinantly produced proteins that correspond to those natively occurring in the ECM material, but perhaps of a different species (e.g. human proteins applied to collagenous ECMs from other animals, such as pigs). The non-native bioactive components may also be drug substances. Illustrative drug substances that may be incorporated into and/or onto the ECM material can include, for example, antibiotics and/or thrombus-promoting substances such as blood clotting factors, e.g. thrombin, fibrinogen, and the like. These substances may be applied to the ECM material as a premanufactured step, immediately prior to the procedure (e.g. by soaking the material in a solution containing a suitable antibiotic such as cefazolin), or during or after positioning of the ECM material around the catheter and/or within the patient.

Submucosa or other ECM material used in embodiments of the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 µg/mg, more preferably less than about 2 µg/mg, and virus levels are preferably less than about 50 plaque forming units (PFU) per gram, more preferably less than about 5 PFU per gram. The ECM material used in embodiments of the invention is preferably disinfected with an oxidizing agent, particularly a peracid, such as peracetic acid. These and additional properties of submucosa or other ECM materials taught in U.S. Pat. No. 6,206,931 may be characteristic of the submucosa used in aspects of the present invention.

In some embodiments, a sheet of biomaterial is wrapped around the interior cuff 150 to accommodate tissue ingrowth.

Turning now to positioning the peritoneal catheter 100 in a body of a patient to begin a medical treatment includes making a small incision in the skin of a medical patient and forming a micropuncture through the rectus muscle and parietal peritoneum of the patient to create a tunnel or opening into the peritoneal cavity. Next an over the wire catheter tube is advanced through the tunnel and a dilator is passed through the tunnel to increase the diameter of the tunnel or dilate out the tunnel. The dilator is removed from the tunnel. Other techniques can be used as are known in the medical field for insertion of a catheter tube into the body of the patient.

Next, a distal end 126 of the catheter tube 112 is advanced through the tunnel of the body of the patient to a target site in a peritoneal cavity of the patient. Next, the stationary flange 114 circumferentially surrounding and mounted on the catheter tube 112 is advanced through the tunnel to a hole in the rectus muscle of the patient. Next, a medical practitioner covers the hole in the rectus muscle of the patient with the stationary flange 114. In one embodiment, the medical practitioner pushes the stationary flange 114 through the hole in the rectus muscle and then pulls the stationary flange 114 back or away from the body of the medical patient to create a seal over the hole. The interior cuff 150 is now positioned in the hole in the rectus muscle. Thereafter the practitioner advances or pushes the mobile flange 116 circumferentially surrounding and positioned on the catheter tube 112 into the body of the patient. Finally, the medical practitioner selectively positions or cinches the mobile flange 116 along the length of the catheter tube 112 adjacent to and in contact with the interior cuff 150 to thereby sandwich the rectus muscle and the interior cuff 150 between the stationary flange 114 and the mobile flange 116. The mobile flange 116 also covers the hole in the rectus muscle to create a seal over the hole to begin a medical treatment or peritoneal dialysis immediately. The peritoneal catheter 100 is immobilized so that the medical treatment can begin immediately by preventing dialysate leakage before the healing and incorporation is completed. No sutures are needed to secure the peritoneal catheter 100 in the medical patient with the use of the stationary flange 114, interior cuff 150, and the mobile flange 116.

Turning now to a third embodiment of a peritoneal catheter 200 illustrated in FIG. 3, the peritoneal catheter 200 is similar in all aspects to the peritoneal catheter 100 described above except for the addition of an outer cuff 270 and two beads 280 mounted on a catheter tube 212. As such, the peritoneal catheter 200 includes a catheter tube 212, a stationary flange 214, a mobile flange 216, and an interior cuff 250. The catheter tube 212, stationary flange 214, mobile flange 216, and interior cuff 250 are similar in all aspects to the catheter tube 112, stationary flange 114, mobile flange 116, and interior cuff 150, respectively, therefore for the sake of brevity these elements will not be described again. Other embodiments may not include any beads 280 or alternatively other embodiments may include a different number of beads 280 or different configuration or arrangement of beads 280.

The outer cuff 270 is mounted on the catheter tube 212 between the mobile flange 216 and a proximal end 224 of the catheter tube 212 wherein the outer cuff 270 is positioned nearer to the interior cuff 250. Typically, the outer cuff 270 is mounted on the catheter tube 212 in a location that would correspond to positioning the outer cuff 270 in the skin layer when the peritoneal catheter 200 is implanted in a medical patient. In one form, the outer cuff 270 is wrapped around an outer surface 218 of the catheter tube 212 to form a tube-like shape that spans between a proximal end 272 and a distal end 274. Alternatively, the outer cuff 270 is formed in a tube shape with an inner diameter that corresponds to the diameter and outer surface 218 of the catheter tube 212. In this alternative embodiment, there is no space or gaps between the inner diameter of the outer cuff 270 and the outer surface 218 of the catheter tube 212. The length of the outer cuff 270 ranges from about 10 millimeters to about 25 millimeters; however other lengths can be used as desired by a medical practitioner. The outer cuff 270 has a wall thickness that spans between the proximal end 272 and the distal end 274.

Turning now to a discussion of materials that can be used in outer cuff 270, such materials can include any suitable biocompatible material. Generally, the material may include synthetic materials, such as a polyester felt, polyethylene terephthalate, polyester, or reconstituted or naturally-derived collagenous materials, or a combination of materials, or any material described above for interior cuff 250.

The beads 280 are positioned on the catheter tube 212 adjacent the interior cuff 250 and between the interior cuff 250 and the mobile flange 216. The beads 280 have a dome-like shape but can be shaped differently in other embodiments such as oval, square, polygonal, barb-like, a nub, or any other shape. The beads 280 are linearly arranged along the longitudinal axis of the catheter tube 212; however the beads 280 can be arranged perpendicular to the longitudinal axis of the catheter tube 212. The beads 280 are positioned at a distance from the interior cuff 250 that is slightly greater than the thickness of the mobile flange 216. The beads 280 are made of a material that is harder than the material used for the mobile flange 216 such that the mobile flange 216 can flex over the beads 280 and snap into position adjacent the interior cuff 250. The beads 280 can be made of silicone or other plastic material.

Turning now to positioning the peritoneal catheter 200 in a body of a patient to begin a medical treatment includes making a small incision in the skin of a medical patient and forming a micropuncture through the rectus muscle and parietal peritoneum of the patient to create a tunnel or opening into the peritoneal cavity. Next an over the wire catheter tube is advanced through the tunnel and a dilator is passed through the tunnel to increase the diameter of the tunnel or dilate out the tunnel. The dilator is removed from the tunnel. Other techniques can be used as are known in the medical field for insertion of a catheter tube into the body of the patient.

Next, a distal end 226 of the catheter tube 212 is advanced through the tunnel of the body of the patient to a target site in a peritoneal cavity of the patient. Next, the stationary flange 214 circumferentially surrounding and mounted on the catheter tube 212 is advanced through the tunnel to a hole in the rectus muscle of the patient. Next, a medical practitioner covers the hole in the rectus muscle of the patient with the stationary flange 214. In one embodiment, the medical practitioner pushes the stationary flange 214 through the hole in the rectus muscle and then pulls the stationary flange 214 back or away from the body of the medical patient to cover and create a seal over the hole. The interior cuff 250 is now positioned in the hole in the rectus muscle. Thereafter the practitioner advances or pushes the mobile flange 216 circumferentially surrounding and positioned on the catheter tube 212 into the body of the patient. Finally, the medical practitioner selectively positions or cinches the mobile flange 216 along the length of the catheter tube 212 adjacent to and in contact with the interior cuff 250 to thereby sandwich the rectus muscle and the interior cuff 250 between the stationary flange 214 and the mobile flange 216. If the beads 280 are present on the catheter tube 212, the mobile flange 216 is pushed over the beads 280 to contact the interior cuff 250 and snap into position against the interior cuff 250. The mobile flange 216 also covers the hole in the rectus muscle to create a seal over the hole to begin a medical treatment or peritoneal dialysis immediately. The peritoneal catheter 200 is immobilized so that the medical treatment can begin immediately by preventing dialysate leakage before the healing and incorporation is completed. No sutures are needed to secure the peritoneal catheter 200 in the medical patient with the use of the stationary flange 214, interior cuff 250, and the mobile flange 216.

While at least one embodiment has been illustrated and described in detail in the drawings and foregoing description, the same is to be considered as illustrative and not restrictive in character, it being understood that the preferred embodiment has been shown and described and that all changes, equivalents, and modifications that come within the spirit of the inventions defined by following claims are desired to be protected. It will be evident from the specification that aspects or features discussed in one context or embodiment will be applicable in other contexts or embodiments. All publications, patents, and patent applications cited in this specification are herein incorporated by reference as if each individual publication, patent, or patent application were specifically and individually indicated to be incorporated by reference and set forth in its entirety herein.

The invention claimed is:

1. A method of positioning a peritoneal catheter in a body of a patient to begin a medical treatment, comprising:
   advancing a distal tip of a catheter tube of the peritoneal catheter through the body of the patient to a target site in a peritoneal cavity of the patient;
   advancing a stationary flange circumferentially surrounding and mounted on the catheter tube through a hole in the rectus muscle of the patient;
   covering the hole in the rectus muscle of the patient with the stationary flange;
   advancing a mobile flange circumferentially surrounding and positioned on the catheter tube into the body of the patient; and
   selectively positioning the mobile flange on the catheter tube to sandwich the rectus muscle between the stationary flange and the mobile flange.

2. The method of claim 1, further comprising:
   the peritoneal catheter includes an interior cuff mounted on the catheter tube adjacent to the stationary flange, the interior cuff located between the stationary flange and the mobile flange; and
   wherein the selectively positioning the mobile flange includes sandwiching the interior cuff between the stationary flange and the mobile flange to resist movement of the peritoneal catheter.

3. The method of claim 2, wherein the selectively positioning the mobile flange includes sliding the mobile flange along a length of the catheter tube to contact the interior cuff.

4. The method of claim 2, further comprising:
   the peritoneal catheter includes an outer cuff mounted on the catheter tube and positioned between the mobile flange and a proximal end portion of the catheter tube.

5. The method of claim 2, wherein the interior cuff comprises harvested extracellular matrix.

6. The method of claim 1, wherein the covering the hole in the rectus muscle of the patient with the stationary flange includes creating a seal over the rectus muscle.

7. A peritoneal catheter, comprising:
   a catheter tube having a proximal end portion opposite a distal end portion;
   a stationary flange attached to the catheter tube near the distal end portion, the stationary flange circumferentially surrounding the catheter tube; and
   a mobile flange positioned on the catheter tube between the stationary flange and the proximal end portion, the mobile flange circumferentially surrounding the catheter tube, the mobile flange configured for selective placement along the catheter tube.

8. The catheter of claim 7, further comprising:
an interior cuff mounted on the catheter tube between the stationary flange and the mobile flange, the interior cuff positioned adjacent the stationary flange.

9. The catheter of claim 8, further comprising:
an outer cuff mounted on the catheter tube and positioned between the mobile flange and the proximal end portion of the catheter tube.

10. The catheter of claim 8, wherein the interior cuff comprises harvested extracellular matrix.

11. The catheter of claim 8, wherein the stationary flange is substantially parallel to the mobile flange when the mobile flange is moved to contact the interior cuff.

12. The catheter of claim 8, wherein the mobile flange is configured to sandwich both the interior cuff and a rectus muscle of a patient between the stationary flange and the mobile flange.

13. The catheter of claim 8, further comprising:
at least one bead positioned on the catheter tube between the interior cuff and the mobile flange wherein the at least one bead is configured to retain the mobile flange adjacent to the interior cuff.

14. The catheter of claim 13, wherein the at least one bead includes two beads positioned in a lineal orientation along a longitudinal axis of the catheter tube.

15. The catheter of claim 13, wherein the at least one bead includes two beads positioned in a substantial perpendicular orientation relative to a longitudinal axis of the catheter tube.

16. The catheter of claim 13, wherein the at least one bead has a hardness greater than the mobile flange.

17. The catheter of claim 13, wherein the at least one bead is configured to retain the mobile flange against the interior cuff.

18. The catheter of claim 8, wherein the interior cuff is made of a biomaterial to accommodate tissue ingrowth.

19. The catheter of claim 8, further comprising:
a sheet of biomaterial wrapped around the interior cuff to accommodate tissue ingrowth.

20. The catheter of claim 8, wherein the interior cuff is made from a wrappable sheet comprising a harvested extracellular matrix that is arranged to be wrapped around a portion of the catheter tube near the distal end portion.

21. The catheter of claim 7, wherein the mobile flange is configured to slide along the catheter tube.

22. The catheter of claim 7, wherein the stationary flange has a fluted disk shape.

23. A peritoneal catheter, comprising:
a catheter tube having a proximal end portion configured to remain exterior of a patient opposite a distal end portion configured to be positioned within a peritoneal cavity of the patient;
an interior cuff mounted on the catheter tube proximal to the distal end portion;
a stationary flange attached to the catheter tube adjacent the interior cuff, the stationary flange positioned between the interior cuff and the distal end portion, the stationary flange circumferentially surrounding the catheter tube; and
a mobile flange positioned on the catheter tube between the interior cuff and the proximal end portion, the mobile flange circumferentially surrounding the catheter tube, the mobile flange configured for selective placement along the catheter tube.

24. The catheter of claim 23, further comprising:
an outer cuff mounted on the catheter tube and positioned between the mobile flange and the proximal end portion of the catheter tube.

25. The catheter of claim 23, wherein the mobile flange is configured to sandwich the interior cuff between the stationary flange and the mobile flange.

* * * * *